(12) United States Patent
Tan et al.

(10) Patent No.: US 10,929,969 B2
(45) Date of Patent: Feb. 23, 2021

(54) METHOD AND APPARATUS FOR MEASURING AND PROFILING ABSORBENT MATERIAL IN AN ABSORBENT ARTICLE

(71) Applicant: AccuSentry, Inc., Marietta, GA (US)

(72) Inventors: Wei Siong Tan, Marietta, GA (US); Stephen Wachtel, Marietta, GA (US); Tjendera Santoso, Marietta, GA (US); Patrick Lizana, Smyrna, GA (US); David Kosen, Marietta, GA (US)

(73) Assignee: AccuSentry, Inc., Marietta, GA (US)

( * ) Notice: Subject to any disclaimer, the term of this patent is extended or adjusted under 35 U.S.C. 154(b) by 139 days.

(21) Appl. No.: 15/247,245

(22) Filed: Aug. 25, 2016

(65) Prior Publication Data

US 2018/0061038 A1    Mar. 1, 2018

(51) Int. Cl.
| | |
|---|---|
| *D04H 1/46* | (2012.01) |
| *A61F 13/534* | (2006.01) |
| *G01N 21/95* | (2006.01) |
| *G01N 21/59* | (2006.01) |
| *G06T 7/00* | (2017.01) |

(Continued)

(52) U.S. Cl.
CPC ...... *G06T 7/0004* (2013.01); *A61F 13/15772* (2013.01); *G06T 7/11* (2017.01); *H04N 5/2256* (2013.01); *A61F 2013/1578* (2013.01); *A61F 2013/15788* (2013.01);

(Continued)

(58) Field of Classification Search
CPC ............. G06T 7/0004; G06T 7/0081; G06T 2207/30124; A61F 13/15772; A61F 2013/1578; A61F 2013/15788; A61F 13/15; A61F 13/534; A61F 13/15634; A61F 2013/530532; A61F 13/15723;

(Continued)

(56) References Cited

U.S. PATENT DOCUMENTS

| | | |
|---|---|---|
| 4,698,832 A | 10/1987 | Kuusi |
| 4,837,715 A | 6/1989 | Ungpiyakul et al. |

(Continued)

OTHER PUBLICATIONS

Extended European Search Report issued for Application No. 17844473.3, dated Jan. 31, 2020.

(Continued)

*Primary Examiner* — Patrick E Demosky
(74) *Attorney, Agent, or Firm* — Meunier Carlin & Curfman LLC

(57) ABSTRACT

Disclosed herein are apparatus, systems and methods of measuring the weight and distribution of the fluff pulp and super absorbent polymer (SAP) or absorbent gelling material (AGM) of absorbent articles. The apparatus may be located at a position after the absorbent cores are formed. Each absorbent article is passed between the light emitter and the camera as well as between the radio transmitter and the radio detector. The camera and radio detector receive the signal transmitted by the light emitter and the radio transmitter respectively through the absorbent articles. The encoder synchronizes the transmission of data by the camera and the radio receiver to the movement of the web. The computer receives the signal data from radio detector and the image data from the camera from each absorbent article and uses the data to determine at least the weight of the fluff pulp and SAP/AGM in the absorbent core.

17 Claims, 7 Drawing Sheets

(51) Int. Cl.
*G06T 7/11* (2017.01)
*A61F 13/15* (2006.01)
*H04N 5/225* (2006.01)
*H04N 5/232* (2006.01)
*H04N 7/18* (2006.01)

(52) U.S. Cl.
CPC .............. *G06T 2207/30124* (2013.01); *H04N 5/23293* (2013.01); *H04N 7/188* (2013.01)

(58) Field of Classification Search
CPC ..... H04N 5/2256; H04N 5/23293; G01J 5/02; G01N 21/95; G01N 21/59; G01N 21/3563
See application file for complete search history.

(56) References Cited

U.S. PATENT DOCUMENTS

| | | | | |
|---|---|---|---|---|
| 5,099,118 | A * | 3/1992 | Francis | G01N 21/86 |
| | | | | 177/1 |
| 5,399,016 | A | 3/1995 | Martin | |
| 6,476,619 | B1 | 11/2002 | Moshe et al. | |
| 7,004,053 | B1 | 2/2006 | Franklin et al. | |
| 8,405,032 | B2 * | 3/2013 | Varga | G01N 21/3563 |
| | | | | 250/339.06 |
| 2002/0071603 | A1 * | 6/2002 | Ungpiyakul | A61F 13/15772 |
| | | | | 382/152 |
| 2003/0119405 | A1 * | 6/2003 | Abuto | A61F 13/15203 |
| | | | | 442/361 |
| 2003/0132762 | A1 * | 7/2003 | Delzer | A61F 13/15658 |
| | | | | 324/663 |
| 2003/0169433 | A1 * | 9/2003 | Koele | A61F 13/15772 |
| | | | | 356/614 |
| 2003/0169904 | A1 * | 9/2003 | Koele | A61F 13/15756 |
| | | | | 382/111 |
| 2004/0083018 | A1 * | 4/2004 | Dollevoet | A61F 13/15772 |
| | | | | 700/109 |
| 2011/0061214 | A1 * | 3/2011 | Wirtz | D01G 25/00 |
| | | | | 28/104 |
| 2012/0150332 | A1 * | 6/2012 | DeBruler | A61F 13/15772 |
| | | | | 700/108 |
| 2013/0181133 | A1 | 7/2013 | Varga et al. | |
| 2014/0163504 | A1 * | 6/2014 | Bianchi | A61F 13/53717 |
| | | | | 604/366 |
| 2014/0169632 | A1 * | 6/2014 | Ogasawara | A61F 13/15658 |
| | | | | 382/103 |
| 2016/0051414 | A1 * | 2/2016 | Piantoni | A61F 13/534 |
| | | | | 264/40.7 |
| 2016/0136009 | A1 | 5/2016 | Weisman et al. | |
| 2017/0296396 | A1 * | 10/2017 | Ricciardi | A61F 13/15699 |

OTHER PUBLICATIONS

Kraszewski, Microwave Aquametry-Needs and Perspectives, IEEE Transactions on Microwave Theory and Techniques, vol. 39, No. 5, May 1991.
International Search Report and Written Opinion issued in Application No. PCT/US17/48570, dated Nov. 7, 2017.

* cited by examiner

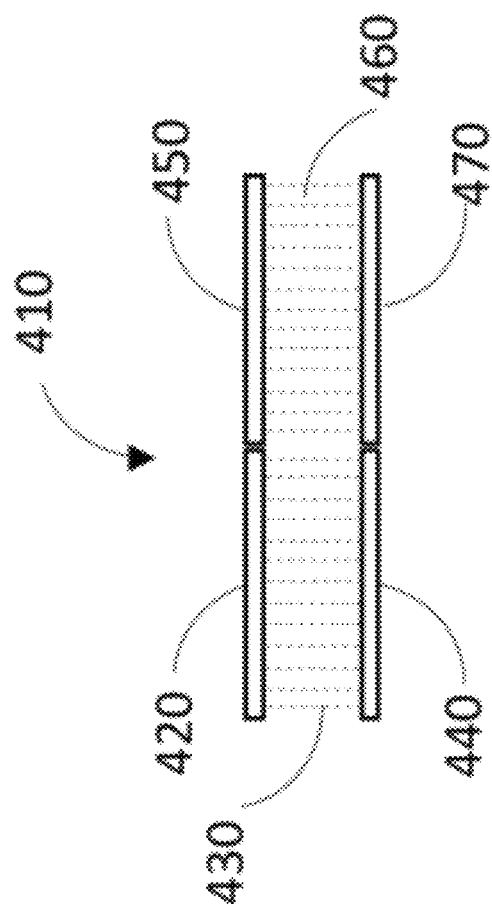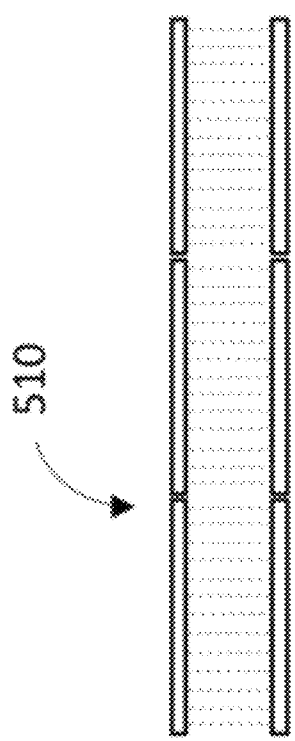
FIG. 4
FIG. 5

METHOD AND APPARATUS FOR MEASURING AND PROFILING ABSORBENT MATERIAL IN AN ABSORBENT ARTICLE

FIELD OF INVENTION

The present invention relates to a method and apparatus for simultaneously measuring and profiling in real-time the weight and the distribution of the fluff pulp and Super Absorbent Polymer (SAP) or Absorbent Gelling Material (AGM) during the production of absorbent articles.

BACKGROUND

Various non-contact measurement techniques have been employed to inspect the quality of a continuously moving web with plurality of components. For example, U.S. Pat. No. 4,698,832 with a priority date of Dec. 1, 1982 describes a procedure and means for non-destructively measuring the distribution of the filler and/or coating materials in the thickness direction of paper or cardboard. Radiation from a radioisotope source is used to excite in the material component its characteristic X-ray radiation, the intensity of this radiation being observed. Measurements are made on both sides of the paper and the contents of other filler components are also determined by X-ray absorption in order to eliminate the effects of these components disturbing the distribution measurement.

U.S. Pat. No. 4,837,715 with a priority date of Jan. 27, 1987 describes a method and apparatus for detecting the placement of components on absorbent material. The patent specifically addresses inspecting the locations of selected elastic members attached to an interconnected plurality of absorbent articles that comprise the web. The patent describes the use of an infrared irradiating light source, a camera to capture the image of the web, and the process for identifying in the image a position of an overlying edge of the composite articles.

U.S. Pat. No. 5,399,016 with a priority date of Oct. 21, 1991 describes a device and method for continuously and non-destructively monitoring variations in the thickness of shaped sections extruded thermoplastic. The invention deploys a detecting and measuring unit connected to a computer system including imaging processing software, a radiation recording unit and a display screen for determining a variation in the thickness of the shaped section based on a variation of emitted radiation detected by the detecting and measuring unit.

U.S. Pat. No. 7,004,053 with priority date of Mar. 15, 2000 describes a system for measuring and controlling cut length of discrete components in a high speed process. The system has the ability to measure the actual cut length, compare the average actual cut length to a target cut length, and to adjust web tension or feed roll speed to achieve the target cut length. Actual cut length variation is thereby reduced.

U.S. Pat. No. 8,405,032 with a priority date of Dec. 16, 2009 describes a method and system for evaluating the distribution of an absorbent material in an absorbent article. The system uses a radiation source and a detector positioned such that the absorbent article is placed between the radiation source and the detector. The radiation source is configured to generate infrared radiation with the wave length between 3 um and 3.2 um. The key to this invention is that SAP/AGM absorbs more infrared radiation within a particular wavelength range than the other materials within the absorbent article. The reduced level of infrared radiation at the detector is indicative of the presence of SAP/AGM in the absorbent article.

WO 2014/170797 with a priority date of Apr. 17, 2013 describes a machine for making absorbent sanitary articles with absorbent pads containing SAP/AGM material. It uses a sensor with microwave resonator to detect the amount of SAP/AGM material. The principle of operation of the microwave resonator to detect the density and moisture of material was described in a scientific paper written by Kraszewski, A. W., Microwave Aquametry-Needs and Perspectives, IEEE Transactions on Microwave Theory and Techniques, vol. 39, no. 5, May 1991. Prior to WO 2014/170797, the principles as described by Kraszewski, A. W. were also applied in U.S. Pat. No. 6,476,619 with a priority date of Aug. 17, 2000 to measure the moisture and density of fibrous yarn, slivers, and pad material.

As described above, there are a number of prior arts that deal with non-contact measurement or inspection techniques for absorbent articles and other types of material using camera and other sensor technologies. Noteworthy, though is that only U.S. Pat. No. 8,405,032 and WO 2014/170797 deal with measuring the SAP/AGM in absorbent articles. The '032 patent describes a method to measure the distribution of the SAP/AGM in absorbent articles using a special mid-wavelength infrared camera with sensitivity between 3 um to 5 um. The '797 patent uses a microwave resonator based on the principles described by Kraszewski, A. W. in a paper published in 1991 to measure the density of the SAP/AGM.

In a high speed production process, manufacturers are facing challenges to control the variations of the quality and distribution of fluff pulp and SAP/AGM in absorbent articles. Traditionally, the way the weight and distribution of fluff pulp and SAP/AGM is roughly determined by quality control personnel who feel the presence of the SAP/AGM with their fingers. Alternatively, but just as manual and subjective, the quality control personnel could first evaluate the fluff pulp density using a light table and then dispense colored liquid onto the absorbent article and subjectively assessing the color intensity distribution across the article. With the light table test, the section where less light passes through the absorbent article is the section where there is the highest concentration of fluff pulp. With the liquid test, the heavier colored section of the absorbent article indicates the section with higher concentration of SAP/AGM. These methods and systems are time intensive, subjective, and prone to mistakes.

Therefore, what is desired are systems, methods, devices, and computer program products that overcome challenges in the art, some of which are described above, for addressing the weight and profiling of the distribution of fluff pulp and SAP/AGM during the manufacture of absorbent articles. This invention describes a method to simultaneously measure and profile in real-time the weight of fluff pulp and SAP/AGM during the production of absorbent articles.

SUMMARY

Disclosed herein are systems, methods, devices, and computer program products for addressing the weight and profiling of the distribution of fluff pulp and SAP/AGM in a high-speed manufacturing process.

Described herein are techniques for measuring the weight and profiling the distribution of the fluff pulp and SAP/AGM that comprise the absorbent core of absorbent articles such as feminine napkins, panty liners, diapers, diaper pants, adult incontinence, bed sheets, puppy pads, and other products incorporating the use of absorbent cores. Variations in the weight of fluff pulp and SAP/AGM from one product to another are inevitable in high speed production lines. The absorbent core is the most important component of the absorbent articles. Therefore, it is extremely valuable to be able to measure the weight and profile the distribution of the SAP/AGM of each absorbent article in real-time. Production personnel can use the real-time data to optimize the weight and distribution of the SAP/AGM.

Also disclosed herein are embodiments of a system for measuring the weight and profiling of the distribution of fluff pulp and SAP/AGM in a high-speed manufacturing process. In one embodiment, the system comprises a light emitter, an image acquisition device such as a camera, a radio frequency (RF) transmitter, a RF receiver, and a computer. The image acquisition device captures an image of an absorbent article with the light emitter emitting light from a side of the absorbent article that is opposite the image acquisition device, thus at least a portion of the light from the light emitter travels through the absorbent article. The absorbent article is placed between the image acquisition device and the light emitter. The section of the acquired image with lower light intensity corresponds to the section of the absorbent article with higher fluff pulp. The presence of SAP/AGM has little or no impact on the intensity of the image. As such, the image intensity provides a good indication of the weight of fluff pulp in the absorbent core. The light emitter can emit light with wavelengths in the UV spectrum (approximately 180-380 nm), visible spectrum (approximately 380-700 nm), or near-infrared spectrum (approximately 700 nm to 2500 nm). The image capture device can continuously capture the images of the absorbent articles as each absorbent article moves between the image capture device and the light emitter. A trigger signal is used to synchronize the image capture operation so that the image capture device captures a complete view of an absorbent core.

The RF receiver receives the radio signal from the RF transmitter. The radio signal can be anywhere between approximately 3 KHz to 3 GHz. The RF signal can be a fixed amplitude or a peak-to-peak voltage (e.g. 10 V). The absorbent article is placed between the RF transmitter and the RF receiver. The amplitude of the radio signal received by the RF receiver is depending on the total weight of fluff pulp and SAP in the absorbent article. The same trigger signal used to synchronize the image capture device is used to synchronize the receiving of the signal by the RF receiver. The trigger signal is used to mark the beginning of an absorbent article. The RF transmitter is continuously transmitting the signal as the absorbent articles glide across it. The RF receiver is continuously sampling the signal level as the absorbent articles glide across it as well. The signal levels across time is proportional to the weight of the SAP/AGM along the travel direction of the absorbent articles. Normally, the absorbent articles are travelling along the length wise direction of the absorbent articles.

In different implementations, two or more RF transmitter and RF receiver pairs may be used with one pair measuring one side of the absorbent articles and another pair measuring the other side of the absorbent articles in the opposite travel direction.

The computer receives the data from the image capture device and the RF receiver. The data from the image capture device is proportional to the weight of fluff pulp between the light emitter and the camera. The data from the RF receiver is proportional to the combined weight of the fluff pulp and SAP/AGM between the RF transmitter and RF receiver. Through calibration, the weight of the fluff pulp and combined fluff pulp and SAP/AGM can be converted to a weight measurement (e.g., grams). The difference between the combined weight of the fluff pulp and SAP/AGM and the weight of the fluff pulp is the weight of the SAP/AGM.

Additional advantages will be set forth in part in the description which follows or may be learned by practice. The advantages will be realized and attained by means of the elements and combinations particularly pointed out in the appended claims. It is to be understood that both the foregoing general description and the following detailed description are exemplary and explanatory only and are not restrictive, as claimed.

BRIEF DESCRIPTION OF THE DRAWINGS

The accompanying drawings, which are incorporated in and constitute a part of this specification, illustrate embodiments and together with the description, serve to explain the principles of the methods and systems:

FIG. 4 shows an exemplary configuration of two RF transmitters and RF receivers;

FIG. 5 shows an exemplary configuration of three RF transmitters and RF receivers;

DETAILED DESCRIPTION

Figure 1:
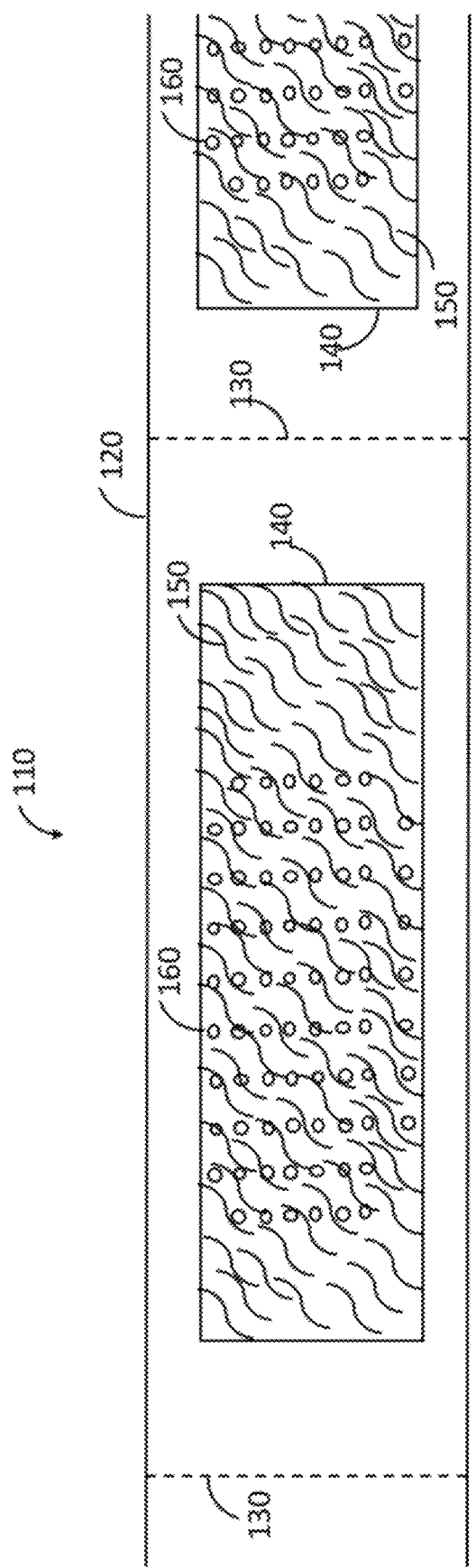
FIG. 1 illustrates a partial top view of an example of fluff pulp and SAP/AGM that comprise the absorbent core of an absorbent article on a continuous web.

Before the present methods and systems are disclosed and described, it is to be understood that the methods and systems are not limited to specific synthetic methods, specific components, or to particular compositions. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal embodiment. "Such as" is not used in a restrictive sense, but for explanatory purposes.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

The present methods and systems may be understood more readily by reference to the following detailed description of preferred embodiments and the Examples included therein and to the Figures and their previous and following description.

As will be appreciated by one skilled in the art, the methods and systems may take the form of an entirely hardware embodiment, an entirely software embodiment, or an embodiment combining software and hardware aspects. Furthermore, the methods and systems may take the form of a computer program product on a computer-readable storage medium having computer-readable program instructions (e.g., computer software) embodied in the storage medium. More particularly, the present methods and systems may take the form of web-implemented computer software. Any suitable computer-readable storage medium may be utilized including hard disks, CD-ROMs, optical storage devices, or magnetic storage devices.

Embodiments of the methods and systems are described below with reference to block diagrams and flowchart illustrations of methods, systems, apparatuses and computer program products. It will be understood that each block of the block diagrams and flowchart illustrations, and combinations of blocks in the block diagrams and flowchart illustrations, respectively, can be implemented by computer program instructions. These computer program instructions may be loaded onto a general purpose computer, special purpose computer, or other programmable data processing apparatus to produce a machine, such that the instructions which execute on the computer or other programmable data processing apparatus create a means for implementing the functions specified in the flowchart block or blocks.

These computer program instructions may also be stored in a computer-readable memory that can direct a computer or other programmable data processing apparatus to function in a particular manner, such that the instructions stored in the computer-readable memory produce an article of manufacture including computer-readable instructions for implementing the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions that execute on the computer or other programmable apparatus provide steps for implementing the functions specified in the flowchart block or blocks.

Accordingly, blocks of the block diagrams and flowchart illustrations support combinations of means for performing the specified functions, combinations of steps for performing the specified functions and program instruction means for performing the specified functions. It will also be understood that each block of the block diagrams and flowchart illustrations, and combinations of blocks in the block diagrams and flowchart illustrations, can be implemented by special purpose hardware-based computer systems that perform the specified functions or steps, or combinations of special purpose hardware and computer instructions.

Described herein are systems, methods and computer-program products for providing useful real-time information about the fluff pulp and SAP/AGM that can be extracted from the image data and/or RF data such as positions, dimensions, and weights to improve the overall consistency and quality of the absorbent pads.

FIG. 1 illustrates sample absorbent cores 140 on a continuous web 110 during the production of absorbent articles such as feminine napkins, panty liners, diapers, diaper pants, adult incontinence, bed sheets, puppy pads, and any other product incorporating the use of absorbent cores. Shown in FIG. 1 is one complete view of an absorbent core 140 followed by a partial view of a second absorbent core. The absorbent cores 140 are typically constructed continuously at speed ranges from approximately 150 meters per minute to approximately 600 meters per minute. Typical production speeds are approximately 500 to 2000 absorbent articles per minute.

Generally, the absorbent cores 140 are comprised of fluff pulp 150 and/or SAP/AGM 160. Both the fluff pulp 150 and SAP/AGM 160 serve as the liquid absorbent agents for the absorbent article. The SAP/AGM 160 possesses much greater liquid absorption capacity than the fluff pulp 150. The absorbent cores 140 are typically sandwiched between two layers of nonwoven webs 120.

In the manufacturing of an absorbent article, it is desired that each absorbent core 140 contains a predetermined weight of fluff pulp 150 and SAP/AGM 160. An insufficient weight of fluff pulp 150 and/or SAP/AGM 160 results in an under-performing absorbent article. Too much fluff pulp 150 and/or SAP/AGM 160 have the potential to cause the absorbent articles to jam the manufacturing process, resulting in costly production stoppages. Also, continuous over-application of even a small weight of fluff pulp 150 and/or SAP/AGM 160 can detrimentally impact business profitability.

Not only is the total weight of fluff pulp 150 and SAP/AGM 160 used in the absorbent core 140 important in the manufacturing of absorbent articles, but the distribution of the fluff pulp 150 and SAP/AGM 160 within the absorbent article may also be important. For example, for an absorbent article designed for a human male, it may be desirable to have a higher concentration of SAP/AGM 160 on the front side of the absorbent article than for an article designed for a female.

FIG. 1 further shows the cut lines 130, which outline the boundaries of adjacent absorbent articles. Generally, it is desired to maintain the position of the absorbent core 140 relative to the cut lines 130.

Figure 2:
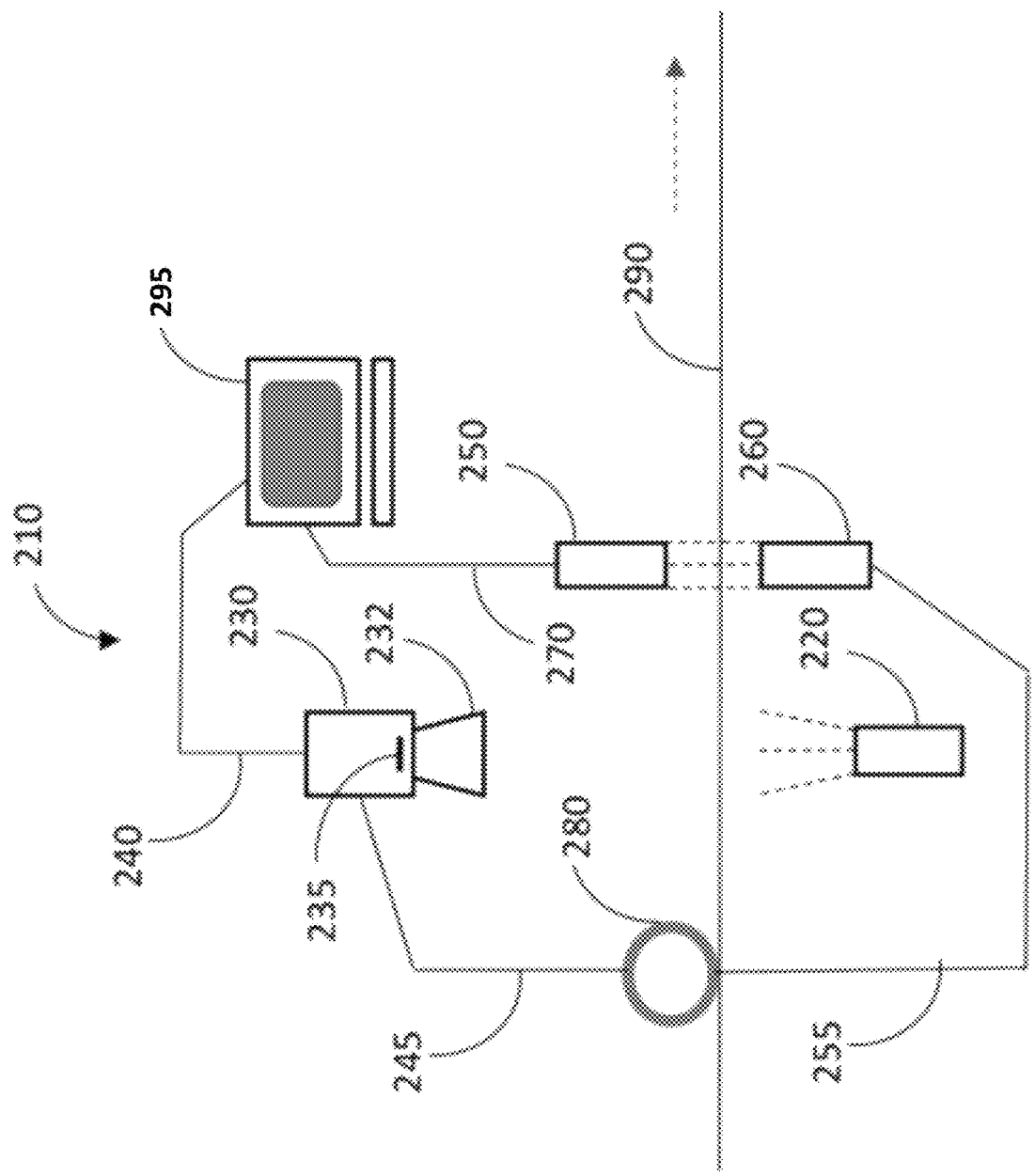
FIG. 2 is an overview illustration of a system configured to implement methods described herein.

FIG. 2 is an overview illustration of a system 210 configured to implement methods described herein. The system 210 of FIG. 2 is comprised of a light emitter 220, an image capture device 230 such as a camera (moving (video) or still), a RF transmitter 250, a RF receiver 260, and an encoder 280. The light emitter 220 and image acquisition device 230 are mounted such that the nonwoven web 290, which carries the absorbent articles, moves between the light emitter 220 and the image acquisition device 230. At least a portion of the light emitted from the light emitter 220 passes through the nonwoven web 290 and the absorbent cores 140 before it reaches a lens 232 of the image capture device 230, which focuses the light onto the camera sensor 235. The encoder 280 tracks the movement of the nonwoven web 290, generating trigger pulses at fixed distance intervals and sending the pulses to the image acquisition device 230 either wirelessly or via an encoder cable 245 (which also includes fiber optic cables as well as normal conductive cables). Each trigger pulse corresponds to a certain distance of web 290 travel. The amount of light energy passing through the absorbent core 140 is proportional to the weight of fluff pulp in the absorbent core 140.

Figure 3:
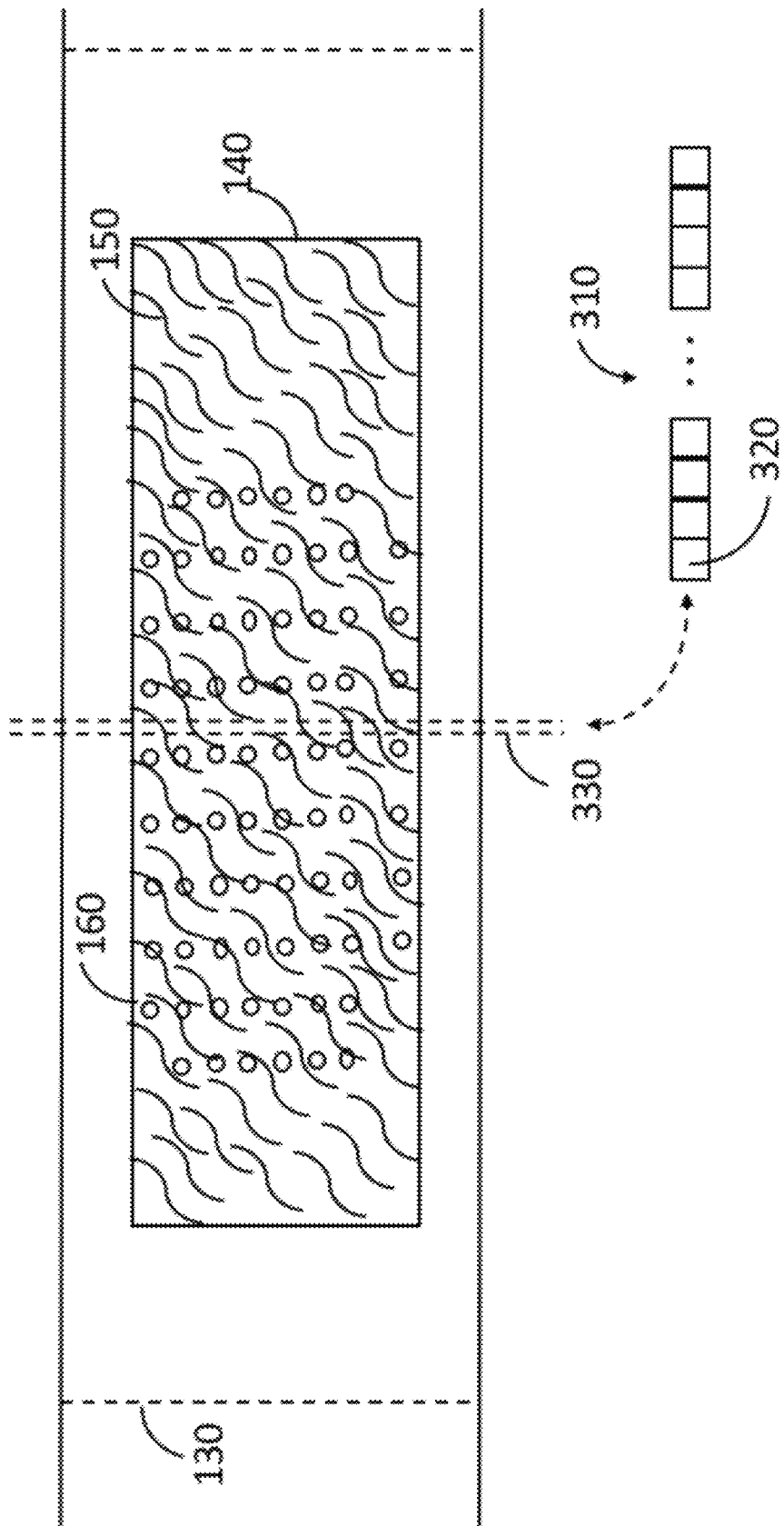
FIG. 3 shows an exemplary pixel configuration of the camera sensor.

FIG. 3 shows an exemplary pixel configuration 310 of the camera sensor 235. At each trigger pulse, pixel 320 represents a profile of a small section of a slice 330 of the absorbent core. A typical configuration of the camera sensor 235 comprises anywhere between approximately 512 to approximately 2048 pixels. As such, the slice of the absorbent core 330 is partitioned into approximately 512 to 2048 segments, generating a complete profile of the slice of the absorbent core.

The image capture device 230 sends one row of data at time to the computer 295 wither wirelessly or via the camera cable 240 for each trigger pulse. The data received by the computer 295 after each trigger pulse is directly correlated to the weight of fluff pulp that is present between the image capture device 230 and the light emitter 230 at the moment of the trigger pulse. The image data collected by the camera sensor 235 on each trigger pulse represents the slice of the absorbent core 140 along the travel direction. The computer 295 is able to construct a full view of the nonwovens web 290 with absorbent core 140 for each absorbent article by piecing together the data from successive slices of absorbent core 140.

The RF transmitter 250 and RF receiver 260 are also positioned such that the nonwovens web 290 runs between the transmitter 250 and the receiver 260, as illustrated in FIG. 2. The RF transmitter 250 transmits radio signal to the RF receiver 260 through the nonwovens web 290 and the absorbent cores 140. The trigger pulses from the encoder 280 are also sent to the RF transmitter 260 wirelessly or via a separate encoder cable 255. The trigger pulse from the encoder 280 activates the RF receiver 260 to send a set of signal data to the computer 295. The signal data is directly correlated to the weight of material that is present between the RF transmitter 250 and RF Receiver 260 at the moment of the trigger pulse.

FIG. 4 shows an exemplary detailed cross sectional configuration 410 of the RF receiver 260 and RF transmitter 250. FIG. 4 further shows two sets of RF transmitter 420, 440 and RF receiver 450, 470 pairs. Each RF transmitter and RF receiver pair senses and determines the weight of the material that is present between the corresponding RF transmitter and RF receiver.

FIG. 5 illustrates an exemplary embodiment that deploys three sets of RF transmitter and RF receiver pairs 510. The more RF transmitter and RF receiver pairs are employed, the more weight data available, and hence the greater the resolution of the apparatus in measuring the weight and distribution in the cross web direction of the absorbent cores, The computer 295 receives a slice of weight data at a time, each slice corresponding to each trigger pulse from the encoder 280. As the web 290 travels, the computer 295 is able to build up a complete weight and distribution profile of the absorbent 140 core along with the web of the absorbent articles. Test data shows that the intensity of the image from the image acquisition device 230 is inversely proportional to the weight of fluff pulp in the absorbent core. As such, the data from the image acquisition device can be used to compute the weight and distribution of fluff pulp 150 on the absorbent cores 140.

Test data further shows that the data received by each RF receiver 260 transmitted by each RF transmitter 250 through the absorbent articles is directly proportional to the weight of the material present between the RF transmitter 250 and RF receiver 260 pair. As a result, the data from the image acquisition device 230 can be used by the computer 295 to compute the weight of and distribution of fluff pulp and SAP/AGM 160 on the absorbent cores 140. By subtracting the total weight of fluff pulp 150 and SAP/AGM 160 computed from the RF receiver 260 data by the weight of fluff pulp 150 computed from the data from the image capture device 230, the computer 295 can then calculate the weight of SAP/AGM 160 in the absorbent core. Therefore, the weight of fluff pulp 150 and SAP/AGM 160 used in the absorbent core 140 of an absorbent article can be reported.

Figure 6:
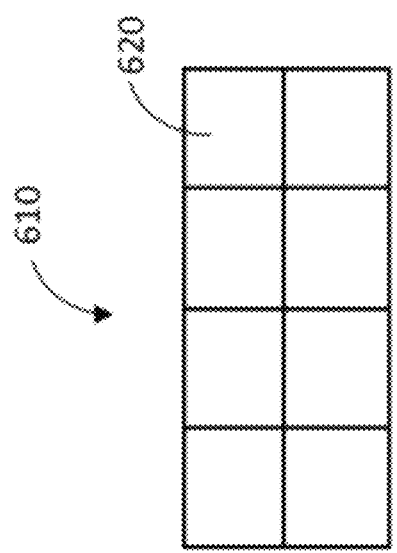
FIG. 6 shows a typical zone pattern for dividing a profile of an absorbent core of an absorbent article into zones.
Figure 7:
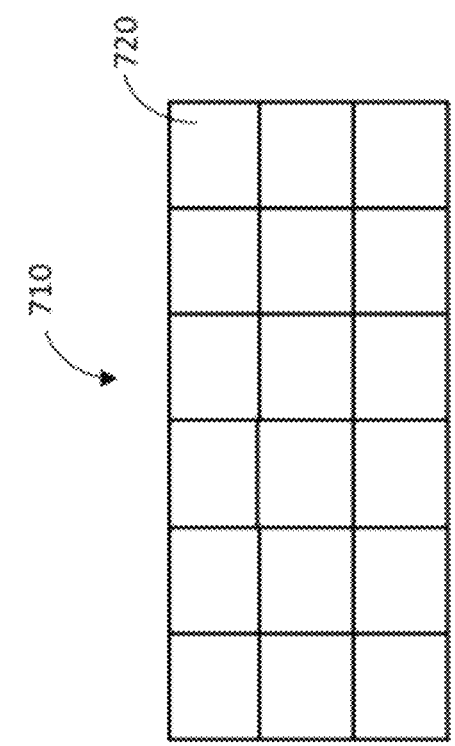
FIG. 7 illustrates a different zone pattern for and absorbent core.

The distribution of the fluff pulp 150 and SAP/AGM 160 as determined by data from the image acquisition device 230 can be reported by zones. FIG. 6 shows a typical zone pattern 610. The fluff pulp 150 and SAP/AGM 160 content of a zone 620 and the other zones is reported individually. FIG. 7 shows a different zone pattern 710 for the absorbent core. Likewise, the fluff pulp 150 and SAP/AGM 160 content of zone 720 and the other zones will be reported individually. In both cases, the computer 295 combines the raw data from the image capture device 230 and the RF receiver 260 to compute the distribution and weight of fluff pulp 150 and SAP/AGM 160 for each zone.

Figure 8:
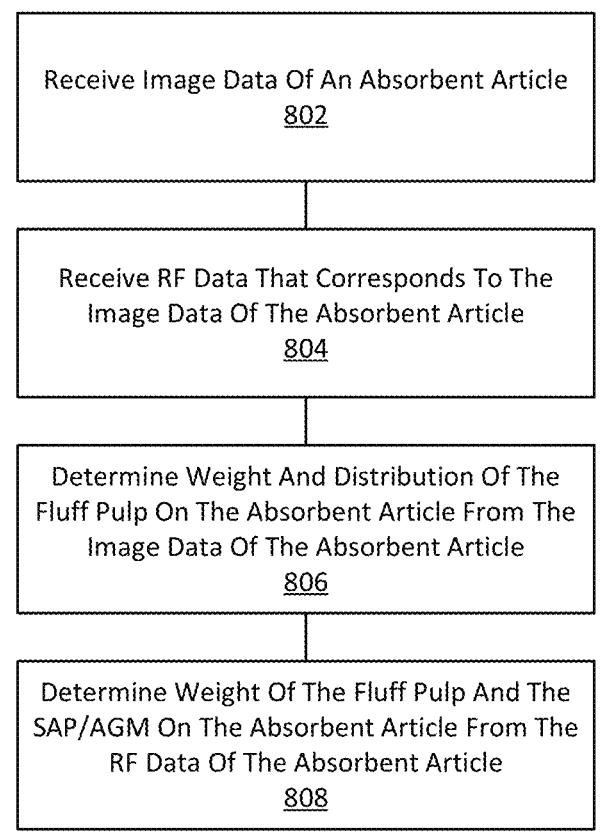
FIG. 8 is a flowchart that illustrates an exemplary method of method of measuring the weight and distribution of the fluff pulp and SAP/AGM of absorbent articles.

FIG. 8 is a flowchart that illustrates an exemplary method of method of measuring the weight and distribution of the fluff pulp and SAP/AGM of absorbent articles. Embodiments of the method comprise 802, receiving, by a computer, image data of an absorbent article. Generally, the image data is provided by an image acquisition device such as a camera. In one aspect, receiving image data of an absorbent article comprises receiving, by the computer, image data of a plurality of slices of the absorbent article, wherein each slice comprises a cross-sectional portion of the absorbent article. At 804, corresponding radio frequency (RF) data of the absorbent article is received by the computer. In one aspect, receiving, by the computer, corresponding radio frequency (RF) data of the absorbent article comprises receiving, by the computer, corresponding RF data for each of the plurality of slices of the absorbent article, wherein the profile of the absorbent article is created from the image data of the plurality of slices of the absorbent article and the corresponding RF data of the plurality of slices of the absorbent article. At 806, the computer is used to determine weight and distribution of the fluff pulp on the absorbent article from the image data of the absorbent article, and at 808, the computer is used to determine weight of the fluff pulp and the SAP/AGM on the absorbent article from the RF data of the absorbent article.

Though not shown in FIG. 8, the method may further comprise determining, by the computer, the weight of the SAP/AGM on the absorbent article by subtracting the weight of the fluff pulp on the absorbent article as determined by the image data from the weight of the fluff pulp and the SAP/AGM on the absorbent article as determined by the RF data. Also not shown in FIG. 8, but the method may also comprise determining, by the computer, the distribution of the fluff pulp and the SAP/AGM on the absorbent article. For example, determining, by the computer, the distribution of the fluff pulp and the SAP/AGM on the absorbent article may comprise creating, by the computer, a profile of the absorbent article from the image data of the absorbent article and the corresponding RF data of the absorbent article; and creating, by the computer, a visual image of the profile of the absorbent article, wherein the visual image indicates the distribution of the fluff pulp and the SAP/AGM on the absorbent article. Determining the distribution of the fluff pulp and the SAP/AGM on the absorbent article MAY further comprise dividing, by the computer, the profile of the absorbent article into a plurality of zones; and indicating the weight and distribution of the fluff pulp and the SAP/AGM in each of the plurality of zones.

In one aspect, the method may further comprise indicating one or more of the weight of the fluff pulp, the weight of the SAP/AGM, or the distribution of the fluff pulp and the SAP/AGM.

Optionally or alternatively the method may include using one or more of the weight of the fluff pulp, the weight of the SAP/AGM, and the distribution of the fluff pulp and the SAP/AGM to control a process for manufacturing the absorbent article.

Also optionally or alternatively, one or more of the weight of the fluff pulp, the weight of the SAP/AGM, and the distribution of the fluff pulp and the SAP/AGM may be used to reject absorbent articles with one or more of the weight of the fluff pulp, the weight of the SAP/AGM, and the distribution of the fluff pulp and the SAP/AGM that are outside predetermined weights or distribution criteria.

The system has been described above as comprised of units. One skilled in the art will appreciate that this is a functional description and that the respective functions can be performed by software, hardware, or a combination of software and hardware. A unit can be software, hardware, or a combination of software and hardware. The units can comprise software for measuring the weight and distribution of the fluff pulp and SAP/AGM of absorbent articles. In one exemplary aspect, the units can comprise a computer 295 that comprises a processor 921 as illustrated in FIG. 9 and described below.

Figure 9:
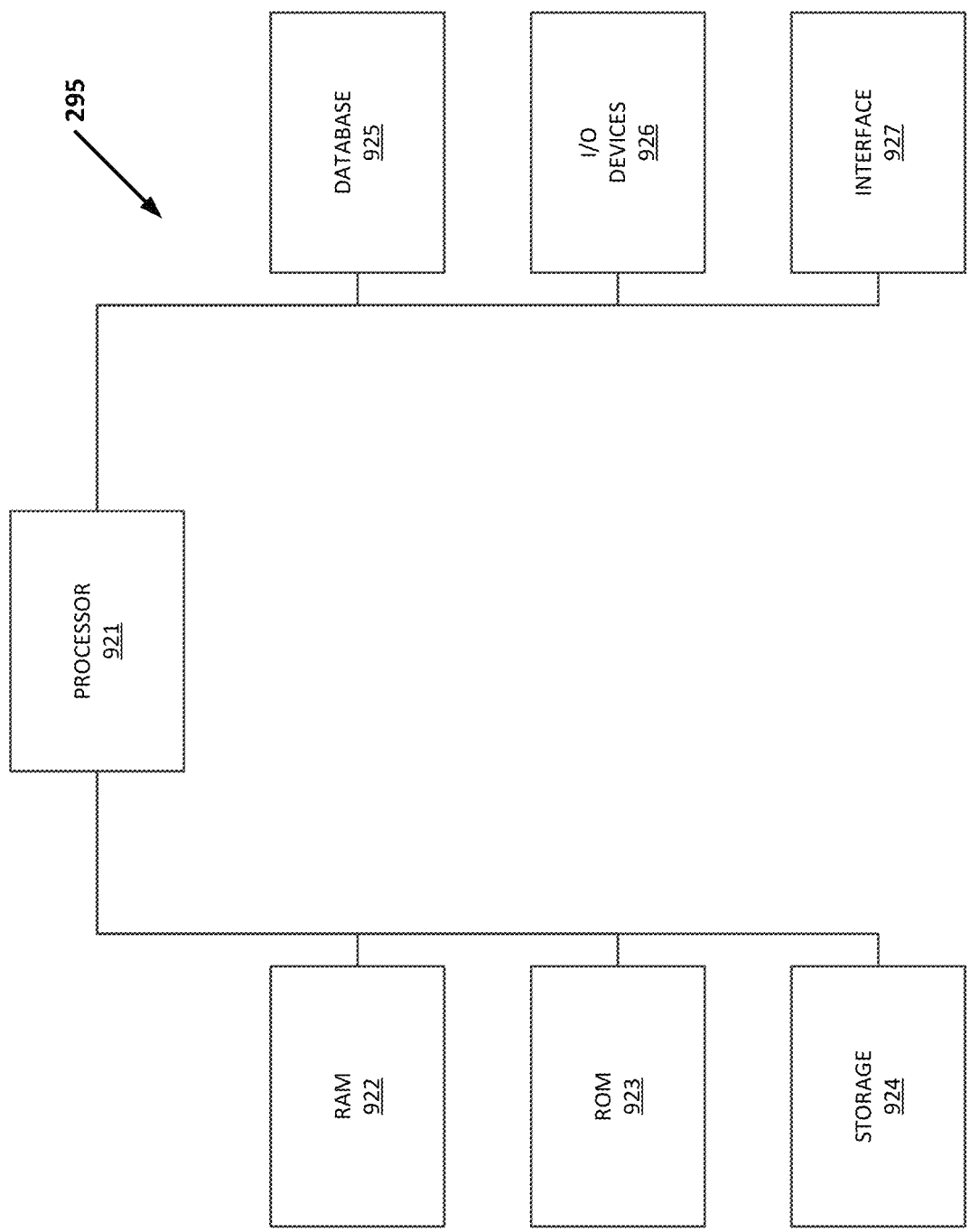
FIG. 9 illustrates an exemplary computer that can be used for measuring the weight and distribution of the fluff pulp and SAP/AGM of absorbent articles.

FIG. 9 illustrates an exemplary computer 295 that can be used for measuring the weight and distribution of the fluff pulp and SAP/AGM of absorbent articles. In various aspects, the computer of FIG. 9 may comprise all or a portion of the computer 295 and/or a process control system. As used herein, "computer" may include a plurality of computers. The computer 295 may include one or more hardware components such as, for example, a processor 921, a random access memory (RAM) module 922, a read-only memory (ROM) module 923, a storage 924, a database 925, one or more input/output (I/O) devices 926, and an interface 927. Alternatively and/or additionally, the computer 295 may include one or more software components such as, for example, a computer-readable medium including computer executable instructions for performing a method associated with the exemplary embodiments. It is contemplated that one or more of the hardware components listed above may be implemented using software. For example, storage 924 may include a software partition associated with one or more other hardware components. It is understood that the components listed above are exemplary only and not intended to be limiting.

Processor 921 may include one or more processors, each configured to execute instructions and process data to perform one or more functions associated with a processing device for measuring the weight and distribution of the fluff pulp and SAP/AGM of absorbent articles. As used herein, "processor" 921 refers to a physical hardware device that executes encoded instructions for performing functions on inputs and creating outputs. Processor 921 may be communicatively coupled to RAM 922, ROM 923, storage 924, database 925, I/O devices 926, and interface 927. Processor 921 may be configured to execute sequences of computer program instructions to perform various processes. The computer program instructions may be loaded into RAM 922 for execution by processor 921.

RAM 922 and ROM 923 may each include one or more devices for storing information associated with operation of processor 921. For example, ROM 923 may include a memory device configured to access and store information associated with computer 295, including information for identifying, initializing, and monitoring the operation of one or more components and subsystems. RAM 922 may include a memory device for storing data associated with one or more operations of processor 921. For example, ROM 923 may load instructions into RAM 922 for execution by processor 921.

Storage 924 may include any type of mass storage device configured to store information that processor 921 may need to perform processes consistent with the disclosed embodiments. For example, storage 924 may include one or more magnetic and/or optical disk devices, such as hard drives, CD-ROMs, DVD-ROMs, or any other type of mass media device.

Database 925 may include one or more software and/or hardware components that cooperate to store, organize, sort, filter, and/or arrange data used by computer 295 and/or processor 921. It is contemplated that database 925 may store additional and/or different information than that listed above.

I/O devices 926 may include one or more components configured to communicate information with a user associated with computer 295. For example, I/O devices may include a console with an integrated keyboard and mouse to allow a user to maintain an algorithm for measuring the weight and distribution of the fluff pulp and SAP/AGM of absorbent articles, software for controlling a manufacturing process for absorbent articles, and the like. I/O devices 926 may also include a display including a graphical user interface (GUI) for outputting information on a monitor. I/O devices 926 may also include peripheral devices such as, for example, a printer for printing information associated with computer 295, a user-accessible disk drive (e.g., a USB port, a floppy, CD-ROM, or DVD-ROM drive, etc.) to allow a user to input data stored on a portable media device, a microphone, a speaker system, or any other suitable type of interface device.

Interface 927 may include one or more components configured to transmit and receive data via a communication network, such as the Internet, a local area network, a workstation peer-to-peer network, a direct link network, a wireless network, or any other suitable communication platform. For example, interface 927 may include one or more modulators, demodulators, multiplexers, demultiplexers, network communication devices, wireless devices, antennas, modems, and any other type of device configured to enable data communication via a communication network.

While the methods and systems have been described in connection with preferred embodiments and specific examples, it is not intended that the scope be limited to the particular embodiments set forth, as the embodiments herein are intended in all respects to be illustrative rather than restrictive.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; the number or type of embodiments described in the specification.

Throughout this application, various publications may be referenced. The disclosures of these publications in their entireties are hereby incorporated by reference into this application in order to more fully describe the state of the art to which the methods and systems pertain.

It will be apparent to those skilled in the art that various modifications and variations can be made without departing from the scope or spirit. Other embodiments will be apparent to those skilled in the art from consideration of the specification and practice disclosed herein. It is intended that the specification and examples be considered as exemplary only, with a true scope and spirit being indicated by the following claims.

What is claimed is:

1. A method of simultaneously measuring weight and distribution of fluff pulp and super absorbent polymer (SAP) or absorbent gelling material (AGM) of absorbent articles during manufacture comprising:
   providing a high-speed manufacturing process for absorbent articles, wherein the high speed manufacturing process produces 500 or more absorbent articles per minute;
   during the manufacturing process and for each of the absorbent articles produced:
   dividing the absorbent article into a plurality of slices, wherein each slice is defined as a portion of the absorbent article between two points, wherein each of the two points are separated along a direction of travel of the absorbent article through the high-speed manufacturing process;
   exposing the plurality of slices of the absorbent article to light energy having a wavelength in the visible spectrum between 380 and 700 nm and capturing light energy that passes through the plurality of slices of the absorbent article as image data, wherein said absorbent article comprises a core of at least fluff pulp and SAP or AGM sandwiched between two layers of nonwoven webs;
   receiving, by a computer, the image data of the plurality of slices of the absorbent article;
   determining, by the computer, an intensity of an image of the absorbent article created from the image data;
   exposing the plurality of slices of the absorbent article to a fixed radio frequency (RF) signal having a frequency between 3 and 30 MHz, and capturing the RF signal that passes through the plurality of slices of the absorbent article as RF data;
   receiving, by the computer, the RF data of the plurality of slices of the absorbent article; and
   determining, simultaneously, by the computer, weight and distribution of the fluff pulp of the absorbent article, weight and distribution of the SAP/AGM of the absorbent article, and weight and distribution of the fluff pulp and the SAP/AGM of the absorbent article based on the intensity of the image of the absorbent article and the corresponding RF data of the absorbent article, wherein the corresponding radio frequency (RF) data of the absorbent article comprises corresponding RF data for each of the plurality of slices of the absorbent article, wherein the profile of the absorbent article is created from the image data of the plurality of slices of the absorbent article and the corresponding RF data of the plurality of slices of the absorbent article.

2. The method of claim 1, wherein determining, by the computer, the weight of the SAP/AGM of the absorbent article comprises subtracting the weight of the fluff pulp of the absorbent article from the weight of the fluff pulp and the SAP/AGM of the absorbent article.

3. The method of claim 1, wherein determining, by the computer, the distribution of the fluff pulp and the SAP/AGM of the absorbent article comprises:
   creating, by the computer, a visual image of the profile of the absorbent article, wherein the visual image indicates the distribution of the fluff pulp and the SAP/AGM on the absorbent article.

4. The method of claim 3, wherein determining, by the computer, the distribution of the fluff pulp and the SAP/AGM of the absorbent article further comprises:
   dividing, by the computer, the profile of the absorbent article into a plurality of zones; and indicating the weight and distribution of the fluff pulp and the SAP/AGM in each of the plurality of zones.

5. The method of claim 1, further comprising indicating one or more of the weight of the fluff pulp, the weight of the SAP/AGM, or the distribution of the fluff pulp and the SAP/AGM.

6. The method of claim 1, wherein one or more of the weight of the fluff pulp, the weight of the SAP/AGM, and the distribution of the fluff pulp and the SAP/AGM are used to control the high-speed manufacturing process for absorbent articles.

7. The method of claim 6, further comprising determining, by the computer, positions and dimensions of the fluff pulp and SAP/AGM of the absorbent article and comparing, in real-time, the positions, dimensions and weights of the fluff pulp and SAP/AGM against target values of positions, dimensions and weights of the fluff pulp and SAP/AGM and using any deviations from the target values to control the high-speed manufacturing process for manufacturing the absorbent articles by steering the positions, dimensions, and weights of the fluff pulp and SAP/SAP to be closer to the targets.

8. The method of claim 7, wherein one or more of the weight of the fluff pulp, the weight of the SAP/AGM, and the distribution of the fluff pulp and the SAP/AGM are used to reject absorbent articles in the high-speed manufacturing process for manufacturing the absorbent articles with one or more of the weight of the fluff pulp, the weight of the SAP/AGM, and the distribution of the fluff pulp and the SAP/AGM that are outside the target values of positions, dimensions and weights of the fluff pulp and SAP/AGM.

9. A system for manufacturing absorbent articles and simultaneously measuring weight and distribution of fluff pulp and super absorbent polymer (SAP) or absorbent gelling material (AGM) of the absorbent articles during a manufacturing process comprised of:
- a system comprising a high-speed manufacturing process for absorbent articles using a moving continuous web, wherein the high speed high-speed manufacturing process produces 500 or more absorbent articles per minute; and
- a system for simultaneously measuring weight and distribution of the fluff pulp and SAP or AGM of each absorbent article produced during the high-speed manufacturing process, said system comprised of:
- a light emitter, wherein the light emitter emits light energy having a wavelength in the visible spectrum between 380 and 700 nm through the absorbent article, wherein said absorbent article comprises a core of at least fluff pulp and SAP or AGM sandwiched between two layers of nonwoven webs;
- an image capture device, wherein the image capture device captures the light energy that passes through the absorbent article;
- a radio frequency (RF) emitter, wherein the RF emitter emits a fixed RF signal having a frequency between 3 and 30 MHz that passes through the absorbent article;
- an RF receiver, wherein the RF receiver receives the RF signal that passes through the absorbent article; and
- an encoder, wherein the encoder synchronizes transmission of image data by the image capture device and RF data by the RF receiver to movement of the continuous web, wherein receiving, by a computer, image data of the absorbent article comprises receiving, by the computer, image data of a plurality of slices of one of the plurality of absorbent articles on the continuous web, wherein each slice comprises a cross-sectional portion of the absorbent article; and wherein receiving, by the computer, corresponding radio frequency (RF) data of the absorbent article comprises receiving, by the computer, corresponding RF data for each of the plurality of slices of the one of the plurality of absorbent articles on the continuous web, wherein the profile of the absorbent article is created from the image data of the plurality of slices of the absorbent article and the corresponding RF data of the plurality of slices of the absorbent article;
- wherein the computer determines weight and distribution of the fluff pulp on the absorbent article, weight of the fluff pulp and the SAP/AGM on the absorbent article, and weight of the SAP/AGM on the absorbent article by:
- receiving image data of the absorbent article from the image capture device;
- determining an intensity of an image of the absorbent article created from the image data;
- receiving corresponding RF data of the absorbent article from the RF receiver;
- simultaneously determining the weight and distribution of the fluff pulp on the absorbent article and the weight of the fluff pulp and the SAP/AGM on the absorbent article from the image data of the absorbent article and the corresponding RF data of the absorbent article.

10. The system of claim 9, wherein determining, by the computer, the weight of the SAP/AGM on the absorbent article comprises subtracting the weight of the fluff pulp on the absorbent article from the weight of the fluff pulp and the SAP/AGM on the absorbent article.

11. The system of claim 9 further comprising a display in communication with the computer, wherein determining, by the computer, the distribution of the fluff pulp and the SAP/AGM on the absorbent article comprises:
- creating, by the computer, a visual image of the profile of the absorbent article on the display, wherein the visual image indicates the distribution of the fluff pulp and the SAP/AGM on the absorbent article.

12. The system of claim 11, wherein determining, by the computer, the distribution of the fluff pulp and the SAP/AGM on the absorbent article further comprises:
- dividing, by the computer, the profile of the absorbent article into a plurality of zones; and indicating, by the computer, the weight and distribution of the fluff pulp and the SAP/AGM in each of the plurality of zones.

13. The system of claim 9, further comprising indicating one or more of the weight of the fluff pulp, the weight of the SAP/AGM, or the distribution of the fluff pulp and the SAP/AGM.

14. The system of claim 9, wherein the computer comprises at least a portion of a control system, wherein the computer controls the high-speed manufacturing process for absorbent articles using one or more of the determined weight of the fluff pulp, the determined weight of the SAP/AGM, and the determined distribution of the fluff pulp and the SAP/AGM.

15. The system of claim 14, wherein the computer compares one or more of the weight of the fluff pulp, the weight of the SAP/AGM, and the distribution of the fluff pulp and the SAP/AGM to predetermined weights or distribution criteria and one or more of the weight of the fluff pulp, the weight of the SAP/AGM, and the distribution of the fluff pulp and the SAP/AGM are used to reject absorbent articles that are outside the predetermined weights or distribution criteria.

16. A computer program product comprising computer-executable computer code sections stored on a non-transitory medium, said computer code sections for measuring weight and distribution of fluff pulp and super absorbent polymer (SAP) or absorbent gelling material (AGM) of absorbent articles, comprising:
- during a high-speed manufacturing process for absorbent articles, wherein the high speed manufacturing process produces 500 or more absorbent articles per minute, and for each of the absorbent articles produced:
- dividing the absorbent article into a plurality of slices, wherein each slice is defined as a portion of the absorbent article between two points, wherein each of the two points are separated along a direction of travel of the absorbent article through the high-speed manufacturing process:
- receiving image data of an absorbent article from each of the plurality of slices of the absorbent article that have been exposed to light energy having a wavelength in the visible spectrum between 380 and 700 nm, wherein each of said absorbent article the plurality of slices of the absorbent article comprises a core of at least fluff pulp and SAP or AGM sandwiched between two layers of nonwoven webs; determining an intensity of an image of the absorbent article plurality of slices of the absorbent article created from the image data;
- receiving corresponding radio frequency (RF) data of the plurality of slices of the absorbent article from a fixed RF signal that passes through the each of the plurality of slices of the absorbent article, wherein the RF signal that passes through the plurality of slices of the absorbent article are between 3 MHz and 30 MHz; determining weight and distribution of the fluff pulp on each of the plurality of slices of the absorbent article, weight of the fluff pulp and the SAP/AGM on the plurality of slices of the absorbent article, and weight of the SAP/AGM on the plurality of slices of the absorbent article based on a combination of the intensity of the image of the absorbent article and the corresponding RF data of the absorbent article; and wherein the weight of the SAP/AGM on the absorbent article is determined by subtracting the weight of the fluff pulp on the absorbent article from the weight of the fluff pulp and the SAP/AGM on the absorbent article, wherein the corresponding radio frequency (RF) data of the absorbent article comprises corresponding RF data for each of the plurality of slices of the absorbent article, wherein a profile of the absorbent article is created from the image data of the plurality of slices of the absorbent article and the corresponding RF data of the plurality of slices of the absorbent article.

17. The computer program product of claim 16, further comprising determining, by the computer, the distribution of the fluff pulp and the SAP/AGM on the absorbent article by: creating a visual image of the profile of the absorbent article, wherein the visual image indicates the distribution of the fluff pulp and the SAP/AGM on the absorbent article.

* * * * *